(12) United States Patent
Higgins et al.

(10) Patent No.: US 6,414,491 B1
(45) Date of Patent: Jul. 2, 2002

(54) AXIAL SAMPLE CONVEYER

(75) Inventors: James A. Higgins, Campbell; Layne E. Howard, Los Gatos, both of CA (US)

(73) Assignee: Varian, Inc., Palo Alto, CA (US)

( * ) Notice: Subject to any disclaimer, the term of this patent is extended or adjusted under 35 U.S.C. 154(b) by 0 days.

(21) Appl. No.: 09/728,470

(22) Filed: Nov. 30, 2000

(51) Int. Cl.$^7$ .................................................. G01V 3/00
(52) U.S. Cl. ....................................... 324/321; 324/318
(58) Field of Search ................................. 324/321, 322, 324/318, 319, 320; 422/65, 64, 62; 436/43

(56) References Cited

U.S. PATENT DOCUMENTS

| | | | |
|---|---|---|---|
| 3,512,078 A | 5/1970 | Hall | 324/321 |
| 5,150,054 A | 9/1992 | Dupree | 324/318 |
| 5,773,296 A * | 6/1998 | Montalbano et al. | 436/43 |
| 5,885,530 A * | 3/1999 | Babson et al. | 422/65 |

* cited by examiner

Primary Examiner—Louis Arana
(74) Attorney, Agent, or Firm—Bella Fishman; Adrei Popovici

(57) ABSTRACT

An axial sample conveyer for transferring samples into an analysis device such as a nuclear magnetic resonance (NMR) probe of an NMR spectrometer includes an auger having a helical thread for axially constraining the samples, and a plurality of guides facing the auger for laterally constraining the samples to follow a linear axial path as the auger is rotated. Samples are inserted into the conveyer through plural input apertures. The samples abut the helical thread of the auger, and are moved through the conveyer as the auger is rotated about its axis. The samples exit the conveyer through corresponding output apertures aligned with the input apertures. Each guide extends between an input aperture and an output aperture.

18 Claims, 3 Drawing Sheets

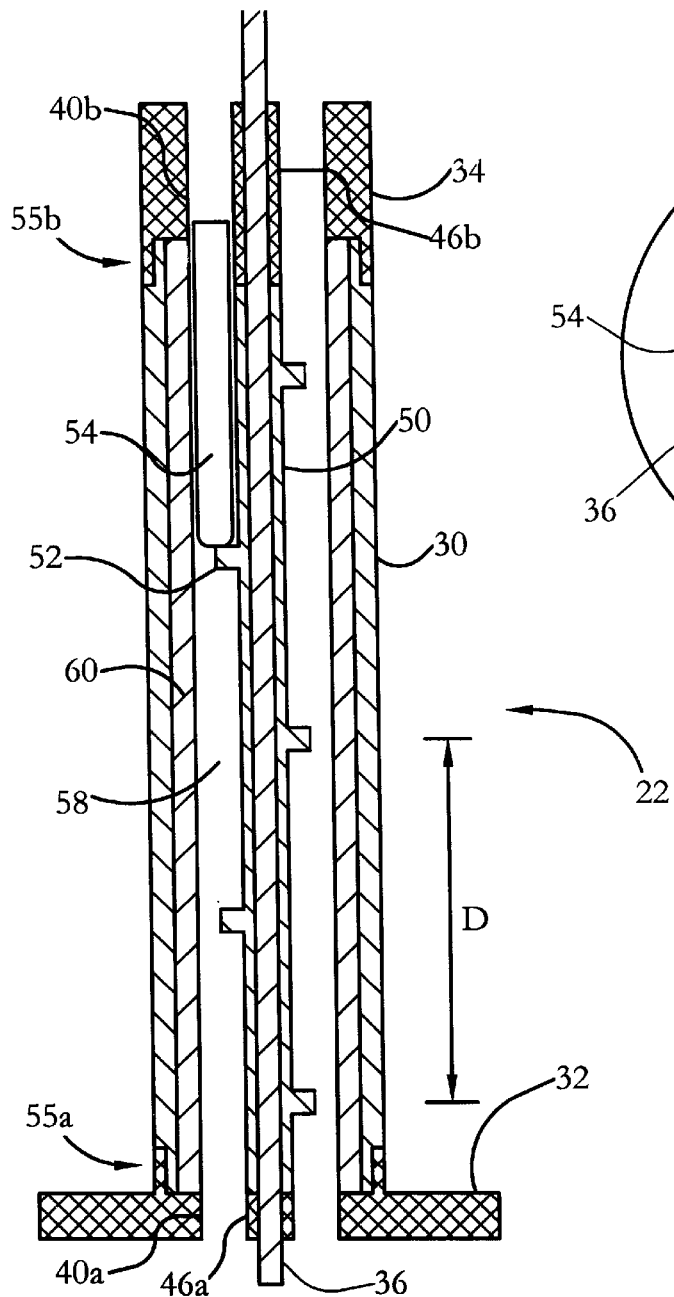
FIG. 3-A
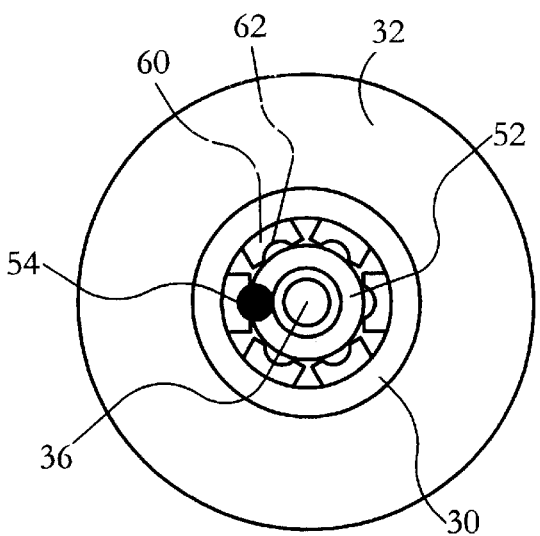
FIG. 3-B
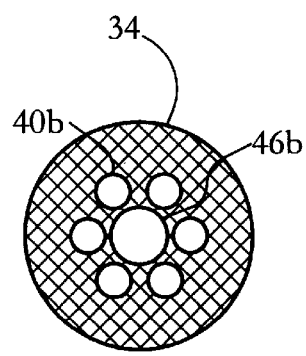
FIG. 3-C

AXIAL SAMPLE CONVEYER

FIELD OF THE INVENTION

The invention in general relates to systems and methods for analyzing samples, and in particular to an axial sample conveyer for inserting sample tubes into an NMR spectrometer.

BACKGROUND OF THE INVENTION

Nuclear magnetic resonance (NMR) spectrometers typically include a superconducting magnet for generating a static magnetic field $B_0$, an NMR probe positioned in a longitudinal bore of the magnet, and a longitudinal guide structure for guiding individual samples of interest into and out of the probe. The direction of the static magnetic field $B_0$ is commonly denoted as the z-axis, while the plane perpendicular to the z-axis is commonly termed the x-y or θ-plane. The terms "longitudinal" and "axial" are used to refer to the z-direction, while the term "transverse" is used to refer to the θ-direction.

Conventional NMR spectrometers typically employ an air-driven system for inserting and ejecting samples in and out of the NMR probe. For a description of a prior art air-driven ejector see for example U.S. Pat. No. 3,512,078, "Gyromagnetic Resonance Spectrometer Employing Air Pressure for Ejecting Samples from the Magnet," by Hall. Such conventional systems can be limited in their sample throughputs.

Improved throughputs for inserting samples into analysis devices can be of use in analysis applications other than NMR spectroscopy, such as for example IR and UV spectroscopy.

SUMMARY OF THE INVENTION

The present invention provides a nuclear magnetic resonance spectrometer including: a magnet for applying a magnetic field to a plurality of nuclear magnetic resonance samples; a nuclear magnetic resonance probe positioned in a bore of the magnet, for performing nuclear magnetic resonance measurements on the samples; an axial multi-sample conveyer coupled to the probe, for transferring a plurality of sample containers containing the samples into the probe; and a driving device coupled to the conveyer, for controlling the motion of the sample containers through the conveyer.

The axial sample conveyer includes: a plurality of input apertures for receiving the sample containers; a plurality of output apertures positioned opposite the input apertures and transversely aligned with the plurality of input apertures, for sequentially transferring the sample containers to the probe; an axially-rotatable auger positioned between the input apertures and the output apertures, for axially constraining a motion of the sample containers between the input apertures and output apertures; and a plurality of axial sample guides positioned facing the auger between the input apertures and the output apertures and transversely aligned with the input apertures and the output apertures, for transversely constraining the motion of the sample containers.

BRIEF DESCRIPTION OF THE DRAWINGS

The foregoing aspects and advantages of the present invention will become better understood upon reading the following detailed description and upon reference to the drawings where:

FIG. 3-A shows a longitudinal sectional view of the conveyer of FIG. 2.

FIG. 3-B shows a top view of the conveyer of FIG. 3-A with its input plate removed.

FIG. 3-C shows a transverse sectional view of the input plate of the conveyer of FIG. 3-A.

DETAILED DESCRIPTION OF THE INVENTION

The following description illustrates embodiments of the invention by way of example and not necessarily by way of limitation.

Figure 1:
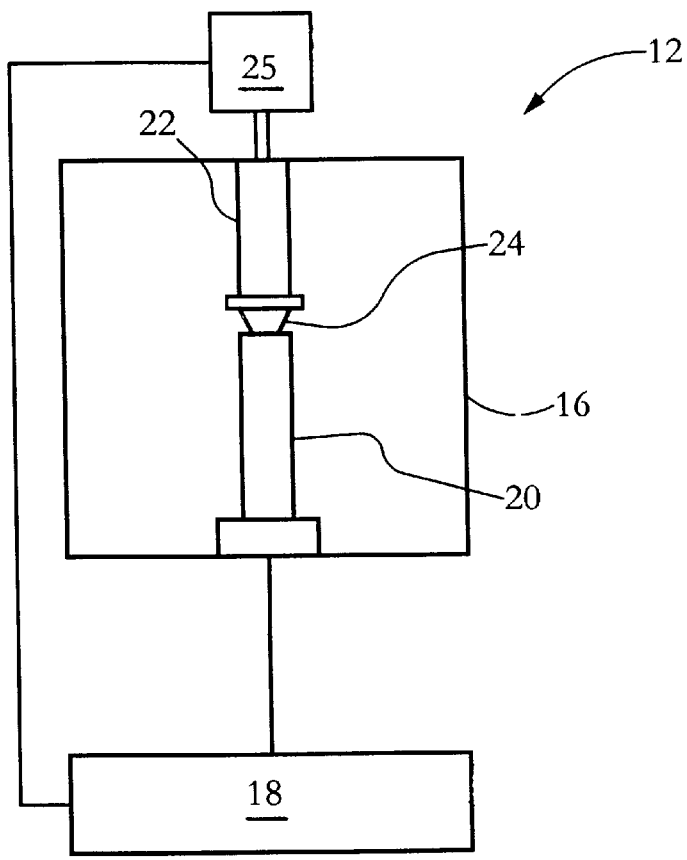
FIG. 1 is a schematic diagram of a nuclear magnetic resonance (NMR) spectrometer according to the preferred embodiment of the present invention.

FIG. 1 is a schematic diagram illustrating a nuclear magnetic resonance (NMR) spectrometer 12 according to the present invention. Spectrometer 12 comprises a magnet 16 for applying a static longitudinal magnetic field $B_0$ to samples of interest. An NMR probe 20 is positioned in a bore of magnet 16. Probe 20 holds one sample container (test tube) at a time within an analysis location situated generally at the center of magnet 16. Each sample container holds a sample of interest. Probe 20 includes one or more radio-frequency (RF) coils for applying radio-frequency transverse magnetic fields $B_1$ to the samples of interest, and/or for measuring the response of the samples to the applied magnetic fields.

A control/acquisition system 18 is electrically connected to magnet 16 and each RF coil of probe 20, and fluidically connected to probe 20. Control/acquisition system 18 applies desired radio-frequency pulses to probe 20, controls the temperature of probe 20, and acquires data indicative of the nuclear magnetic resonance properties of the samples within probe 20. Control/acquisition system 18 is further electrically connected to a driving device 25, described in more detail below, for controlling the operation of driving device 25. Driving device 25 is preferably a non-magnetic device, such that the driving device does not produce magnetic fields which could otherwise disturb NMR measurements performed on samples within probe 20. Suitable non-magnetic driving devices include piezo-electric motors and devices employing fluid flow.

An axial multi-sample conveyer 22 is coupled to probe 20, for sequentially transferring a plurality of sample containers to probe 20. Conveyer 22 is preferably positioned above probe 20, such that samples exiting conveyer 22 drop into probe 20 due to gravity. Conveyer 22 is connected to probe 22 through a funnel 24 positioned underneath conveyer 22, between conveyer 22 and probe 20. Funnel 24 is positioned with a larger input aperture facing conveyer 22 and a smaller output aperture facing probe 20. The input aperture of funnel 24 is sufficiently large to capture all sample containers exiting conveyer 22. The diameter of the output aperture of funnel 24 is preferably comparable to or slightly larger than the diameter of each sample container, such that each sample container is accurately directed into the analysis location of probe 20.

Figure 2:
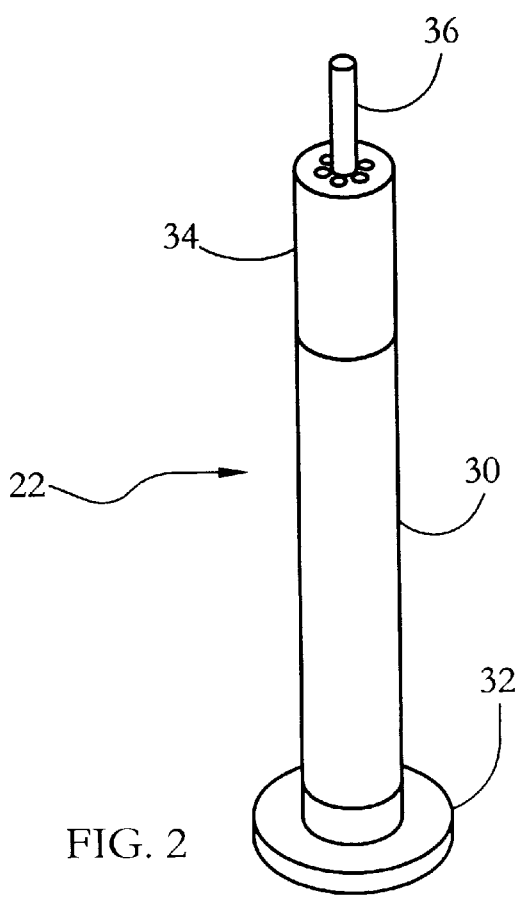
FIG. 2 shows an isometric view of an axial sample conveyer of the spectrometer of FIG. 1 according to the preferred embodiment of the present invention.

FIG. 2 shows an isometric view of conveyer 22 according to the preferred embodiment of the present invention. Conveyer 22 comprises a fixed output (base) plate 32, a lateral cylindrical casing 30 mounted on base plate 32, a fixed input (top) plate 34 mounted on casing 30 opposite output plate 32, and an axially-rotatable rigid shaft 36 mounted through bearings on plates 32 and 34.

FIG. 3-A shows a longitudinal sectional view of conveyer 22, while FIG. 3-B shows a top view of conveyer 22 with its input plate 34 removed. As illustrated in FIG. 3-A, output plate 32 has a plurality of axial sample output apertures 40a defined therethrough, for allowing sample containers to pass from conveyer 22 into funnel 24 (shown in FIG. 1). Referring to FIG. 3-A, output apertures 40a are arranged along output plate 32 at the same radial distance from the longitudinal axis of conveyer 22.

Input plate 34 has a corresponding plurality of axial sample input apertures 40b defined therethrough, for allowing sample containers into the interior of conveyer 22. Each input aperture 40b is transversely aligned with and of the same size as a corresponding output aperture 40a. Each input aperture 40b is positioned above a corresponding output aperture 40a. The transverse cross-section of each aperture 40a–b is preferably circular, as illustrated by the transverse cross-section of input plate 34 shown in FIG. 3-C. The size of each aperture 40a–b is preferably comparable to the diameter of each sample container 54, such that each sample container 54 fits axially through apertures 40a–b.

Casing 30 is attached to input and output plates 32, 34 along annular longitudinal overlap regions 55a–b, respectively. Casing 30 overlaps with input plate 32 over region 55a, and with output plate 34 over region 55b. Input and output plates 32, 34 laterally enclose casing 30 along overlap regions 55a–b, respectively. Transverse (radial) screws can be inserted through casing 30 and plates 32, 34 along overlap regions 55a–b, for attaching plates 32, 34 to casing 30.

Referring back to FIG. 3-A, shaft 36 is mounted on bearings 46a–b, which form parts of plates 32, 34 respectively. Shaft 36 extends axially through plates 32, 34. Shaft 36 is further connected to driving device 25, for rotating shaft 36 around its longitudinal axis.

Figure 4:
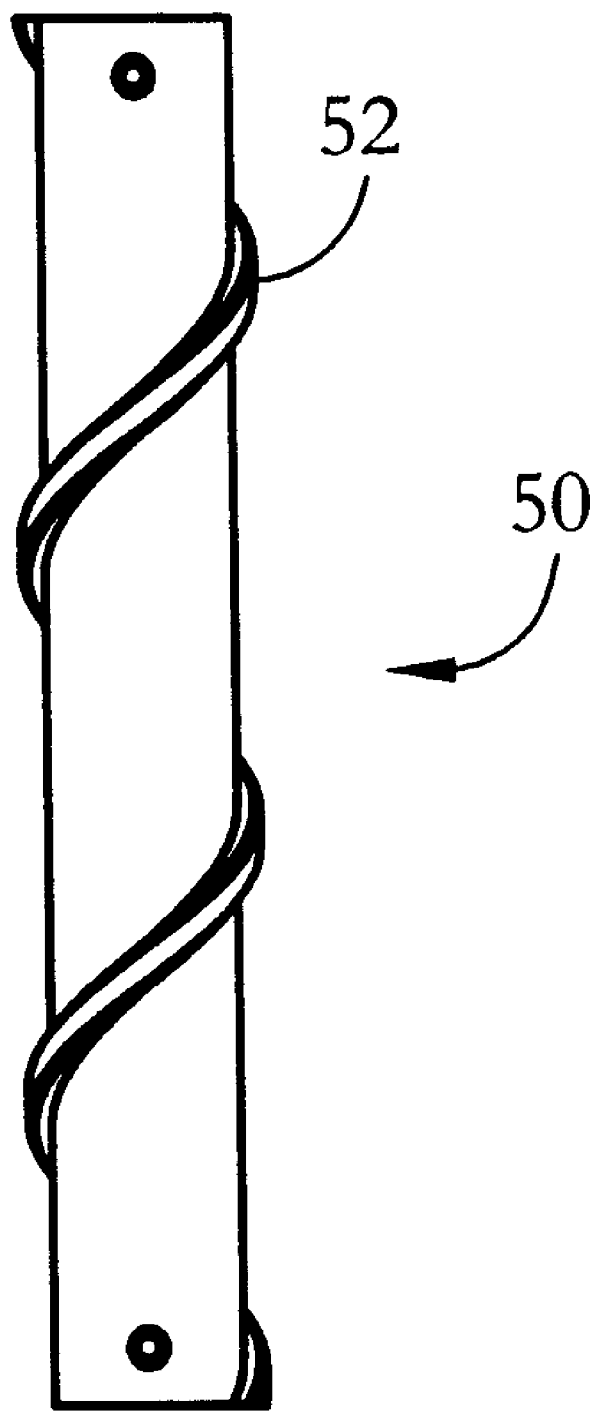
FIG. 4 shows a front view of an auger of the conveyer of FIG. 2, according to the present invention.

An axial auger (Archimedes screw) 50 is mounted on shaft 36. Auger 50 extends between input plate 34 and output plate 32. Auger 50 has a helical thread or flange 52 extending away from the central body of auger 50, for axially (vertically) constraining a plurality of sample containers 54. Thread 52 is illustrated in a lateral view in FIG. 4. Referring back to FIG. 3-A, the transverse extent of thread 52 is less than the full diameter of each sample container 54, such that at least part of each sample container 54 extends outside of thread 52. The transverse extent of thread 52 is at the same time sufficiently large to support and axially constrain each sample container 54. The axial separation or period D of thread 52 is larger than the axial extent of each sample container 54, such that each sample container 54 fits between consecutive turns of thread 52.

As shown in FIGS. 3-A and 3-B, conveyer 22 further includes a plurality of axial guides 60 extending between input plate 34 and output plate 32. For ease of manufacturing, guides 60 are preferably formed by discrete rails attached by screws to the inside surface of casing 30. Guides 60 can also be integrally formed as depressions along the inside surface of casing 30. Each guide 60 has a guiding surface 62 facing auger 50, for transversely constraining sample containers 54 to follow a linear axial path along guide 60 as auger 50 is rotated. The transverse cross-section of each guiding surface 62 can be flat or curved, e.g. shaped as an arc of a circle. Each guiding surface 62 laterally encloses and constrains containers 54. A passage 58 is defined between each guiding surface 62 and the central portion of auger 50. Each passage 58 connects an input aperture 40b to a corresponding output aperture 40a, for allowing passage of sample containers 54 from input aperture 40b to output aperture 40a. connects an input aperture 40b to a corresponding output aperture 40a, for allowing passage of sample containers 54 from input aperture 40b to output aperture 40a.

Funnel 24 and the various components of axial sample conveyer 22 are made of non-magnetic materials that do not affect NMR measurements taken on samples within probe 20 (shown in FIG. 1). As is apparent to the skilled artisan, suitable non-magnetic materials can include plastics, glasses, aluminum, and stainless steel. In a present implementation, shaft 36 is made of aluminum, auger 50 is made of white nylon, and casing 30, input plate 34, output plate 32 and guides 60 are made of clear acrylic.

The loading of sample containers 54 into probe 20 will now be described with reference to FIGS. 1 and 3-A. During the operation of spectrometer 20, multiple sample containers 54 are transferred into conveyer 22 through input apertures 40b, shown in FIG. 3-A. Sample containers 54 entering conveyer 22 then rest onto thread 52. Thread 52 axially constrains sample containers 54, and controls the passage of containers 54 through conveyer 22.

To move containers 54 down through conveyer 22, driving device 25 is used to rotate shaft 36 at a desired rate. The rotation of shaft 36 causes the rotation of auger 50. As auger 50 is rotated, the z-coordinate of thread 52 at each guide (θ-) location decreases at a constant rate. Sample containers 54 move down along a linear, vertical trajectory defined by guides 60 at a rate controlled by the rotation of auger 50. Sample containers 54 exit sequentially through output apertures 46a, and one by one pass through funnel 24 (shown in FIG. 1) and into an analysis location within probe 20. The analysis location holds one sample container at a time. The insertion of each sample container 54 into probe 20 is controlled by the rotation of auger 50. Desired NMR measurements are performed on each individual sample within probe 20. After each 360° rotation of auger 50, a new set of six sample containers 54 is inserted into conveyer 22. Each sample container 54 is transversely constrained by a corresponding guide 60 to follow a linear axial trajectory corresponding to a fixed θ-location. Used sample containers are allowed to fall out of probe 20 through the bottom in a conventional manner.

The above-described system and methods allow relatively high throughputs for transferring samples in and out of the measurement location of the spectrometer. New sample containers 54 can be inserted into probe 20 at intervals ranging from seconds to minutes or longer. In a presently-envisioned application, a new sample container 54 is inserted into probe 20 every 30 seconds.

Conveyer 20 is preferably assembled from manufactured components as described below with reference to FIG. 3-A. Auger 50 is attached to shaft 36 using screws. Each guide 60 is using screws. Shaft 36 is then fitted through the central aperture and bearing 46a of output plate 32. Input plate 34 is slipped onto shaft 36 through its central aperture and bearing 46b.

It will be clear to one skilled in the art that the above embodiments may be altered in many ways without departing from the scope of the invention. For example, the number of sample container conduits/guides can be higher or lower than the number six illustrated above. The sample container guides can be formed integrally in the interior surface of a casing, rather than as individual rails. A sample storage enclosure can be positioned above the sample conveyer, opposite the probe relative to the conveyer. The sample storage enclosure can include plural axial bores aligned with the input apertures of the conveyer, for storing sample containers and transferring the sample containers into the conveyer. The sample conveyer can be placed underneath the probe, or can form part of the probe. Suitable applications of the conveyer may include applications other than NMR and other spectroscopy applications. Accordingly, the scope of the invention should be determined by the following claims and their legal equivalents.

What is claimed is:

1. A nuclear magnetic resonance spectrometer comprising:
   a) a magnet for applying a magnetic field to a plurality of nuclear magnetic resonance samples;
   b) a nuclear magnetic resonance probe positioned in a bore of the magnet, for performing nuclear magnetic resonance measurements on the samples; and
   c) an axial multi-sample conveyer coupled to the probe, for transferring a plurality of sample containers containing the samples into the probe, the conveyer comprising:
      a plurality of input apertures for receiving the sample containers,
      a plurality of output apertures positioned opposite the input apertures and transversely aligned with the plurality of input apertures, for sequentially transferring the sample containers to the probe,
      an axially-rotatable auger positioned between the input apertures and the output apertures, for axially constraining a motion of the sample containers between the input apertures and output apertures, and
      a plurality of axial sample guides positioned facing the auger between the input apertures and the output apertures and transversely aligned with the input apertures and the output apertures, for transversely constraining the motion of the sample containers.

2. The spectrometer of claim 1 wherein:
   a) the conveyer comprises a lateral casing enclosing the auger; and
   b) each of the plurality of guides is formed by a rail attached to an inside surface of the casing.

3. The spectrometer of claim 1 wherein:
   a) the conveyer comprises a lateral casing enclosing the auger; and
   b) each of the plurality of guides is formed by an inside surface of the casing.

4. The spectrometer of claim 1 wherein the conveyer further comprises:
   a) a fixed input plate comprising an axial input bearing coupled to the auger, the input apertures being defined in the input plate; and
   b) a fixed output plate comprising an axial output bearing coupled to the auger, the output apertures being defined in the output plate.

5. The spectrometer of claim 1 further comprising a driving device coupled to the auger, for rotating the auger.

6. The spectrometer of claim 5 wherein the driving device comprises a piezoelectric motor coupled to the auger.

7. The spectrometer of claim 5 wherein the driving device comprises a gas source for providing gas flow coupled to the auger, for rotating the auger.

8. The spectrometer of claim 1 wherein:
   a) the sample conveyer is positioned above the probe; and
   b) the motion of the sample containers through the conveyer is driven by gravity.

9. The spectrometer of claim 8 further comprising a funnel positioned between the output apertures and the probe, for funneling the sample containers from the output apertures to the probe.

10. An axial multi-sample conveyer for providing a plurality of sample containers to a nuclear magnetic resonance probe, comprising:
    a) a plurality of input apertures for receiving the sample containers;
    b) a plurality of output apertures positioned opposite the input apertures and transversely aligned with the plurality of input apertures, for sequentially transferring the sample containers to the probe;
    c) an axially-rotatable auger positioned between the input apertures and the output apertures, for axially constraining a motion of the sample containers between the input apertures and output apertures; and
    d) a plurality of axial sample container guides positioned facing the auger between the input apertures and the output apertures and transversely aligned with the input apertures and the output apertures, for transversely constraining the motion of the sample containers.

11. The conveyer of claim 10 wherein:
    a) the conveyer comprises a lateral casing enclosing the auger; and
    b) each of the plurality of guides is formed by a rail attached to an inside surface of the casing.

12. The conveyer of claim 10 wherein:
    a) the conveyer comprises a lateral casing enclosing the auger; and
    b) each of the plurality of guides is formed by an inside surface of the casing.

13. The conveyer of claim 10 further comprising:
    a) a fixed input plate comprising an axial input bearing coupled to the auger, the input apertures being defined in the input plate; and
    b) a fixed output plate comprising an axial output bearing coupled to the auger, the output apertures being defined in the output plate.

14. An axial multi-sample conveyer for providing a plurality of sample containers to a nuclear magnetic resonance probe, comprising:
    a) a rotating axial helical thread for engaging the samples and axially constraining a motion of the samples; and
    b) a plurality of axial sample guides each facing the thread, for transversely constraining the motion of the samples to a linear axial trajectory.

15. A method of transferring a plurality of sample containers to a nuclear magnetic resonance probe, comprising the steps of:
    a) axially moving the sample containers by engaging the sample containers with a helical thread and rotating the helical thread; and
    b) transversely constraining the sample containers to axial trajectories by enclosing each sample container with an axial guide facing the thread.

16. A nuclear magnetic resonance spectrometer comprising:
    a) a magnet for applying a magnetic field to a plurality of nuclear magnetic resonance samples;
    b) a nuclear magnetic resonance probe positioned in a bore of the magnet, for performing nuclear magnetic resonance measurements on the samples;

c) an axial multi-sample conveyer positioned above the probe and facing the probe, for transferring a plurality of sample tubes containing the samples into the probe, the conveyer comprising:
- a plurality of upper input apertures for receiving the sample tubes,
- a plurality of lower output apertures positioned below the input apertures and transversely aligned with the plurality of input apertures, for sequentially transferring the sample tubes to the probe,
- an axially-rotatable auger positioned between the input apertures and the output apertures, for axially controlling a downward motion of the sample tubes between the input apertures and output apertures, and
- a plurality of axial sample guides positioned facing the auger between the input apertures and the output apertures and transversely aligned with the input apertures and the output apertures, for transversely constraining the downward motion of the sample tubes;

d) a driving device coupled to the auger, for rotating the auger; and e) a funnel positioned between the output apertures and the probe, for funneling the sample tubes from the output apertures downward into the probe.

17. An axial multi-sample conveyer for transferring a plurality of sample containers to an analysis device, comprising:

a) a plurality of input apertures for receiving the sample containers;

b) a plurality of output apertures positioned opposite the input apertures and transversely aligned with the plurality of input apertures, for sequentially transferring the sample containers to the analysis device;

c) an axially-rotatable auger positioned between the input apertures and the output apertures, for axially constraining a motion of the sample containers between the input apertures and output apertures; and d) a plurality of axial sample container guides positioned facing the auger between the input apertures and the output apertures and transversely aligned with the input apertures and the output apertures, for transversely constraining the motion of the sample containers.

18. A method of inserting a plurality of sample containers into an analysis device, comprising the steps of:

a) axially moving the sample containers by engaging the sample containers with a helical thread and rotating the helical thread; and b) transversely constraining the sample containers to axial trajectories by enclosing each sample container with an axial guide facing the thread.

* * * * *